US007147847B2

(12) United States Patent
De Simone

(10) Patent No.: US 7,147,847 B2
(45) Date of Patent: *Dec. 12, 2006

(54) USE OF BACTERIA ENDOWED WITH ARGININE DEIMINASE TO INDUCE APOPTOSIS AND/OR REDUCE AN INFLAMMATORY REACTION AND PHARMACEUTICAL OR DIETETIC COMPOSITIONS CONTAINING SUCH BACTERIA

(75) Inventor: Claudio De Simone, Ardea RM (IT)

(73) Assignee: VSL Pharmaceuticals, Inc., Gaithersburg, ND (US)

( * ) Notice: Subject to any disclaimer, the term of this patent is extended or adjusted under 35 U.S.C. 154(b) by 129 days.

This patent is subject to a terminal disclaimer.

(21) Appl. No.: 10/400,675

(22) Filed: Mar. 28, 2003

(65) Prior Publication Data

US 2003/0215429 A1    Nov. 20, 2003

Related U.S. Application Data

(62) Division of application No. 09/601,533, filed as application No. PCT/IT98/00275 on Oct. 13, 1998, now Pat. No. 6,572,854.

(30) Foreign Application Priority Data

Feb. 20, 1998  (IT)  ............... RM98A0103

(51) Int. Cl.
*A61K 38/46*  (2006.01)
(52) U.S. Cl. .................. 424/93.45; 424/94.6; 424/780; 435/252.9
(58) Field of Classification Search ............. 424/93.45, 424/94.6, 780; 435/252.9
See application file for complete search history.

(56) References Cited

U.S. PATENT DOCUMENTS 4,415,550 A  *  11/1983  Pakhomov et al.
5,196,195 A       3/1993   Griffith
5,419,901 A  *   5/1995   Griffith
5,599,795 A       2/1997   McCann et al.

FOREIGN PATENT DOCUMENTS

EP    0 414 007 A    2/1991
EP    0 508 701 A    10/1992
WO    WO 95 32720 A  12/1995

OTHER PUBLICATIONS www.fda.gov/fdac/features/2002/302_gums.html; accessed Feb. 17, 2005.*
Liu et al. (Applied and Environmental Microbiology (1995), vol. 61, No. 1, pp. 310-316).*
Manca de Nadra et al, "Isolation and properties of Arginine Deiminase in *Lactobacillus buchneri* NCD0110". *J. Appl. Biochem.*, vol. 6, 1984, pp. 184-187.
Takaku et al, "Anti-tumor activity of arginine deiminase from mycoplasma arginini and its growth-inhibitory mechanism", *Jpn. J. Cancer Res.*, vol. 86, No. 9, Sep. 1995, pp. 840-846.
Narita et al, "L-Arginine may mediate the therapeutic effects of low protein diets", *Proceedings of the National Academy of Sciences of USA.*, vol. 92, May 1995, pp. 4552-4556.
Manca de Nadra et al, "Arginine dehydrolase pathway in *Lactobacillus buchneri*: a review", *BIOCHIMIE*, vol. 70, 1988, pp. 367-374.

* cited by examiner

*Primary Examiner*—Susan Coe Hoffman
(74) *Attorney, Agent, or Firm*—Nixon & Vanderhye P.C.

(57) ABSTRACT

Disclosed is the use of bacteria endowed with arginine deiminase to induce apoptosis and/or reduce an inflammatory reaction, and pharmaceutical or dietetic compositions containing such bacteria. Also disclosed is a strain of *Lactobacillus brevis* highly endowed with arginine deiminase.

7 Claims, No Drawings

USE OF BACTERIA ENDOWED WITH ARGININE DEIMINASE TO INDUCE APOPTOSIS AND/OR REDUCE AN INFLAMMATORY REACTION AND PHARMACEUTICAL OR DIETETIC COMPOSITIONS CONTAINING SUCH BACTERIA

This application is a division of application Ser. No. 09/601,533 filed Aug. 3, 2000 now U.S. Pat. No. 6,572,854 which in turn is a §371 of PCT/IT98/00275 filed Oct. 13, 1998, the entire content of which is hereby incorporated by reference in this application.

The present invention concerns the use of bacteria endowed with arginine deiminase to induce apoptosis and/or reduce an inflammatory reaction, and pharmaceutical or dietetic compositions which contain such bacteria. The invention also concerns a strain of *Lactobacillus brevis* which is highly endowed with arginine deiminase.

The balance between the cell population in an organism can be controlled by way of regulating the rate of proliferation or differentiation or death of the constituent cells (Collins, M. K. L. et al. A, *Trends Biochem. Sci.* 18:307, 1993). Cell death during embryogenesis, metamorphosis, hormone-dependent tissue atrophy and the normal turnover of the tissues is referred to as "programmed cell death". For the large part that event takes place by way of "apoptosis", a process which is characterised by condensation and segmentation of the nucleus, condensation and fragmentation of the cytoplasm and often fragmentation of the chromosomic DNA into nucleosomal units (Schwartz, L. M. et al *Immunol. Today* 14:582. 1993). Apoptosis in the development of vertebrates often occurs when the cells do not receive the extracellular survival signals necessary to suppress an intrinsic cell suicide programme; the survival factors can be produced by the surrounding cells of different type (paracrine mechanism) or of the same type (autocrine mechanism). Apoptosis occurs during embryonic development in particular in complex organs where a given cell sub-population is killed. For example many neurons move in the brain during development, just as auto-reactive T lymphocytes are eliminated in the interior of the thymus. In an adult apoptosis occurs in particular in tissues which are subjected to reversible expansion as in the hormone-dependent cells of the breast and the prostate gland after removal of the hormone or following cytokine-dependent expansion of the haemopoietic cells of the bone marrow.

The modifications which occur in the cell in the course of apoptosis have been widely studied and described (Cohen, J. J. et al *Lab. Clin. Med.* 124:761. 1994). Apoptosis is clearly different from necrosis which corresponds to the modifications which occur when cell death derives from cell damage. In necrosis in fact the damaged cells swell up and burst, releasing their intracellular content which is toxic in relation to other cells of the tissue, and triggering off an inflammatory response. In contrast phagocytosis of the apoptotic bodies is so fast as not to induce dispersion of the cellular contents in the extracellular space which otherwise would cause perilesional phlogosis typical of necrosis.

Recent experimental evidence indicates that alterations in cell survival contribute to the pathogenesis of many human diseases including cancer, viral infections, auto-immune diseases, neurovegetative disorders and AIDS (Thompson. C. B. *Science* 267:1456, 1995). A treatment aimed at specifically altering apoptosis can have the potential to modify the natural progression of some of those diseases. Both chemotherapy agents and radiation induce the death of tumour cells primarily causing damage to the DNA which in turn causes cell suicide. In addition many tumours conserve some of the physiological cell death control systems which are characteristic of the cells from which they originate. For example cancer of the prostate and cancer of the breast are respectively androgen- and oestrogen-dependent. Therefore anti-androgenic therapy in the treatment of cancer of the prostate gland or removal of oestrogens by means of anti-oestrogens such as tamoxifen in the course of breast cancer are fundamental and universally accepted procedures. Both those methods induce apoptosis in the tumour cells which are otherwise respectively dependent for their survival on androgens or oestrogens. In addition the beneficial effects of glucocorticoids observed in subjects with lymphoidal leukaemia can be attributed to the induction of apoptosis: other substances used for chemotherapy of cancer such as cyclophosphamide, metotrexate, etoposide and cisplatin induce apoptosis of tumour cells (Thatte, U. et al Apoptosis, *Drugs* 54:511. 1997).

Previous studies have shown that lactic bacteria present in foods and/or in dietetic/pharmaceutical formulations can cause transitory colonisation of the intestine and have beneficial effects. Survival during the intestinal transit or adhesion to the epithelium seem to be is important for modifying the immune response of the host (Schiffrin, E. J. et al *Am. J. Clin. Nutr.* 66: 515S, 1997). The potentially beneficial effects of lactic bacteria include protection from enteric infections, stimulating the secretion of IgA, and inhibition of the growth of intestinal carcinoma, strengthening the activity of IgA. T-cells and macrophages (Perdigon, G. et al *J. Dairy Sci.* 78:1597. 1995). In vitro, lactic bacteria have revealed a capacity to stimulate the production of alpha TNF, interleukin (IL)-6 and IL-10 on the part of human mononuclear cells, even to an extent greater than that revealed when using lipopolysaccharide (LPS) as a stimulating agent, confirming a potentiating action on non-specific immunity of the host (Miettinen, M. et al *Infect. Immun.* 64:5403. 1996). Still in vitro, lactic bacteria have demonstrated a capacity to absorb mutagenic substances present in cooked foods, confirming the observation that the administration of lactobacilli in man reduces the excretion of mutagenic substance after the ingestion of fried meat and thus the risk of cancer of the colon (Lidbeck, A. et al Eur. *J. Cancer Prev.* 1:341, 1992). Experiments conducted with fermented milk with *Bifidobacterium infantis, Bifidobacterium bifidum, Bifidobacterium animalis, Lactobacillus acidophilus,* or *Lactobacillus paracasei* on the growth of breast tumour cells MCF7 have demonstrated that the various fermented milks are capable, even if to varying degrees, of inhibiting the growth of tumour cells. The anti-proliferative effect cannot be correlated to the presence of the bacteria in the fermented milk to the milk or to the fractions thereof; the hypothesis is for the presence of a soluble compound produced ex novo from the lactic bacteria during fermentation of the milk or microbial transformation of some components of the milk into a biologically active form (Biffi, A. et al *Nutr. Cancer* 28:93, 1997).

Many micro-organisms use arginine as a source of carbon, nitrogen and energy. Arginine deiminase transforms arginine in the presence of water into citrulline and ammonia. That enzymatic procedure has been encountered in a variety of pathogenic or potentially pathogenic bacteria such as *Pseudomonas* sp and *Bacillus* sp, and in some types of mycoplasms. It has been demonstrated that this system plays a part in oral ecology, in protecting less acid-tolerant organisms during the fall in the pH to 4, or even lower values, in dental plaque, during glycolysis caused by bacteria which are more resistant to acidity (Curran, T. M. *Appl. Environ. Microbio.* 61:4494, 1995).

Studies have been conducted on arginine deiminase which can be obtained from mycoplasms, to be used as a cure for cancer (Takaku, H. et al *Jpn. J. Cancer Res.* 1:840. 1995). Mycoplasms are micro-organisms which are similar to bacteria which, unlike the latter, lack a cell wall and the genome of which is around ⅙ of that of *E. coli:* however they can be pathogenic for man, animals and for plants and in addition they cannot be easily handled due to the absence of a cell wall. Purification was thus implemented in respect of the enzyme arginine deiminase which can be obtained from mycoplasms, which behaves like an immunogen and which is not free from undesired effects if used in vivo (McGarrity, J. G. et al U.S. Pat. No. 5,372,942). Other micro-organisms endowed with arginine deiminase (such as for example *Pseudomonas* sp and *Bacillus* sp) cannot be used by virtue of their potential pathogenicity and pyrogenicity.

We have now surprisingly found that some bacteria are rich in arginine deiminase, in particular some Gram-positive bacteria and some Gram-negative bacteria, and also some strains of lactic bacteria, in particular of the species *Lactobacillus brevis* or *Lactobacillus fermentum*, more particularly the strain of *Lactobacillus brevis* referred to as CD2 deposited with the DSM—Deutsche Sammlung von Mikroorganismen und Zellkulturen GmbH, Brunswick, Germany, under the access number DSM 11988, are capable of inducing apoptosis and can therefore be used for prevention or therapy in respect of clinical situations characterised by insufficient or absent apoptosis or by inflammation.

The above-mentioned bacteria have surprisingly shown an arginine deiminase capable of inducing apoptosis and they can be used as such or after suitable lyophilisation or also after sonication. Indeed in accordance with the present invention the bacteria in question can be live or sonicated and the level of concentration can fluctuate from $1\times10^1$ CFU to $1\times10^{13}$ CFU per gram of composition, according to the desired effect and the amount of arginine deiminase which they have. The same bacterial strains can be used to reduce or terminate an inflammatory reaction caused by nitric oxide (NO). NO which is synthesised from L-arginine by means of nitric oxide synthase (NOS) is an intra- and intercellular messenger with numerous biological actions. Alterations in the level of synthesis of NO are at the basis of numerous other physiopathological conditions such as arterial hypertension, renal insufficiency, septic shock, vasodilation induced by hypoxia, vasospasm resulting from subarachnoid haemorrhage, neuronal destruction in vascular infarction and other neurodegenerative conditions, chronic inflammatory pathologies, anaphylaxis and immunodeficiency. Arginine deiminase converts arginine into citrulline and $NH_3$ without the production of nitric oxide and can thus have an anti-inflammatory and curative or remedial effect, for example in intestinal malabsorption and pancreatic insufficiency with modulation for example of the metabolic and/or nutritional state of the subject. An effect which is referred to by way of non-limiting example can be that of reducing the levels of oxalates and/or phosphates in blood and urine.

Non-limiting examples of diseases or disorders which can be treated and/or prevented by using bacteria which are rich in arginine deiminase are tumours in general in particular colon-rectal cancer, cancer of the liver, gliomae, neuroblastomae, squamocellular oral carcinoma, lymphoid tumours, cancer of the prostate gland, cancer of the bladder, cancer of the breast, cancer of the pleura and the peritoneum, serious myasthenia, systemic lupus erythematosus, and other autoimmune diseases including those of the thyroid, diseases characterised by acute and/or chronic inflammatory processes, is bronchial asthma, intestinal inflammatory diseases, gastrites, duodenites, gastric ulcers, duodenal ulcers, pneumonias and pleurisies, infections from adenovirus, baculovirus and in general supported by a viral agent, diseases characterised by acute and/or chronic inflammatory and/or degenerative processes of the central and/or peripheral nervous system, pancreatites, endomyocardites and ischaemic damage (myocardial, retinal, cerebral and renal), urolithiases, nephrocalcinoses, hyperoxaluria, hyperphosphaturia, nephroalteration in the systemic and/or district arterial and/or venous pressure such as portal hypertension, vaginoses and vaginites, procto-haemerrhoidal inflammations, prostates, sinusites and otites, conjunctivites, gingivites, periodontopathy, anaphylactic phenomena and immunodeficiencies.

Such micro-organisms which are rich in arginine deiminase can be used individually or in combination with each or with other lactic bacteria such as *Lactobacillus acidophilus, Lactobacillus buchneri, Lactobacillus casei, Lactobacillus catenaforme, Lactobacillus cellobiosus, Lactobacillus crispatus, Lactobacillus curvatus, Lactobacillus delbrueckii, Lactobacillus jensenii, Lactobacillus leichmanii, Lactobacillus minutus, Lactobacillus plantarum, Lactobacillus rogosae, Lactobacillus salivarius, Bifidobacterium adolescentis, Bifidobacterium angulatum, Bifidobacterium bifidum, Bifidobacterium breve, Bifidobacterium catenulatum, Bifidobacterium dentium, Bifidobacterium eriksonii, Bifidobacterium infantis, Bifidobacterium longum, Bifidobacterium plantarum, Bifidobacterium pseudo-catenulatum, Bifidobacterium pseudolongum, Streptococcus lactis, Streptococcus raffinolactis, Streptococcus thermophilus, Acidaminococcus ferments, Cytophaga fermentans, Rhodoferax fermentans, Cellulomonas fermentans* and *Zymomonas mobilis*.

Still in accordance with the present invention the bacteria can be used in association with arginine deiminase, sphingomyelinase or other enzymes, with cortisone, anti-inflammatory, immuno-modulant, cytostatic, immunological, endocrinological, vascular, anaesthetic, and vasodilatory drugs, growth factors, cytokines, ceramides, vitamins and minerals, lipids, amino acids and carbohydrates, formulations for enteric use and dietetic, prebiotic or probiotic supplements, and with excipients commonly used in the pharmaceutical industry or in the foodstuffs/dietetic field. The preferred form of administration is orally but it is not limitative in relation to possible topical, rectal, nasal or parenteral administration. The composition of the invention will thus be in the form of pills or tablets, capsules, globuli, suppositories, emulsions, suspensions, stick-on plasters, creams, ointments, sprays, collyria, collutoria or dentifrices.

The following examples which are set forth by way of non-limiting illustration will illustrate the present invention in greater detail.

EXAMPLE 1

Induction of Apoptosis in Various Cellular Systems

Cells used:
1 Normal:
 PBL (human peripheral blood lymphocytes)
 HS27 (normal human fibroblasts)
 HaCaT (eternalised normal human keratinocytes)
2. Tumoral:
 Jurkat (human T leukaemia)
 P815 (murine mastocytoma)
 J744 (murine tumoral macrophages)

The cells were cultivated in suitable medium with serum (10%) at 37° C. (5% $CO_2$) for 18–72 hours in the presence or absence of sonicated preparations in buffered solution of phosphates (PBS) of L. brevis (final concentration in the cellular suspensions: 100 mg/10 ml). At the end of the incubation operation the cells were counted and vitality determined on the basis of exclusion of the dye tripan blue. Possible induction of death by apoptosis in the cells treated with the bacteria was determined on the basis of:

morphology under an optical microscope after colouring with haematoxylin/eosin.

colouring with acridine orange/ethidium bromide detected by means of fluorescence microscopy and cytofluorimetry, and detection of DNA laddering by means of agarose gel electrophoresis of the DNA.

TABLE 1

| | Apoptosis (%) | |
|---|---|---|
| | Controls | L. brevis (CD2) |
| PBL | 0 | 0 |
| HS27 | 0 | 0 |
| HaCaT | 0 | 0 |
| Jurkat | 2–3 | 15–20 |
| P815 | 0 | 1–3 |
| J744 | 0 | 1–3 |

The above-reported results indicate clearly that treatment for 14–18 hours with sonicated bacteria of the invention determines the induction of significant levels of apoptosis in tumoral cells, while not giving rise to any effect on the normal cell systems analysed.

EXAMPLE 2

Demonstration of the Presence of Arginine Deiminase in Bacterial Strains

The activity of arginine deiminase in some bacterial strains was determined on the basis of conversion in an aqueous solution of radio-marked arginine into citrulline and $NH_3$. The presence of suitable inhibitors (L-N-nitro-arginine methyl ester HCl and L-valine) capable of specifically inhibiting other enzymes which effect conversion of the arginine (nitric oxide synthase and arginase respectively) made it possible to attribute the enzymatic activity determined to the arginine deiminase and not to other enzymes. In addition the use of a specific inhibitor in respect of arginine deiminase (formamidine) made it possible to confirm the soundness of the results.

TABLE 2

Activity of arginine deiminase (expressed as pmol of radioactive citrulline produced/mg bacterial proteins per minute

| Bacterium strain | pmol citrulline/mg proteins/min |
|---|---|
| L. brevis CD2 | 6.72 |
| L. fermentum | 0.46 |
| L. casei | 0.13 |
| L. acidophilus | 0.002 |
| L. plantarum | 0.05 |
| B. bifidum | 0.03 |
| S. thermophilus | 0.020 |

Bacterial strains are considered as useful for the purposes of the present invention, which have values of greater than 0.1 pmol is citrulline/mg bacterial proteins/min.

The presence of inhibitors of nitric oxide synthase (L-NAME, L-nitromonomethyl arginine) or arginase (L-valine) did not in any way influence the enzymatic activity in regard to conversion of arginine to citrulline, thus making it possible to attribute the generation of citrulline observed with the various bacteria to the arginine deiminase. In addition the absence in the analysis system of calcium and calmodulin which are indispensable in terms of the activity of the constituent nitric oxide synthase did not in any way modify the activity in terms of conversion of the arginine on the part of bacteria, further confirming that the enzyme responsible for the latter is arginine deiminase.

The results set out hereinafter demonstrate that the activity of arginine deiminase encountered in the bacteria in question was further capable of completely inhibiting both the activity of constituent nitric oxide synthase (NOS) and that of inducible NOS, probably because the presence thereof involves deprivation of the substrate (arginine) of the various forms of nitric oxide synthase. For that purpose rat cerebellum extracts and rat peritoneal macrophages stimulated in vitro with lipopolysaccharide of E. coli (100 mg/ml) and interferon (100 U/ml) respectively were used as positive controls for constituent NOS and for inducible NOS.

TABLE 3

Activity of constituent and inducible nitric oxide synthase and arginine deiminase

| Sample | Citrulline (pmol/5 microlitres) |
|---|---|
| Cerebellum | 0.24 |
| Cerebellum + L-NAME | 0.01 |
| Cerebellum + calcium chelating agent (EGTA) | 0.01 |
| Cerebellum more inhibitor of calmodulin (W13) | 0.01 |
| Cerebellum + L. brevis CD2 (5 micrograms) | 0.72 |
| Cerebellum + L. brevis CD2 + L-NAME | 0.8 |
| Cerebellum + L. brevis CD2 + EGTA | 0.74 |
| Cerebellum + L. brevis CD2 + W13 | 0.76 |
| Cerebellum + L. fermentum (30 microgrammes) | 0.38 |
| Cerebellum + L. fermentum + L-NAME | 0.4 |
| Cerebellum + L. fermentum + EGTA | 0.4 |
| Cerebellum + L. fermentum + W13 | 0.39 |
| Untreated macrophages | 0 |
| Macrophages + LPS + IFN | 0.32 |
| Macrophages + LPS + IFN + L-NAME | 0 |
| Macrophages + L. brevis CD2 (5 micrograms) | 0.76 |
| Macrophages + L. brevis CD2 + L-NAME | 0.78 |
| Macrophages + LPS + IFN + L. brevis CD2 | 0.81 |
| Macrophages + LPS + IFN + L. brevis CD2 + L-NAME | 0.82 |
| Macrophages + L. fermentum (30 micrograms) | 0.4 |
| Macrophages + L. fermentum + L-NAME | 0.41 |
| Macrophages + LPS + IFN + L. fermentum | 0.42 |
| Macrophages + LPS + IFN + L. fermentum + L-NAME | 0.4 |

It seems to be evident that not all the bacteria have an enzymatic activity in respect of arginine deiminase of a significant level for the purposes of the present invention (Table 2) and that the strains which are endowed therewith inhibit both constituent NOS and inducible NOS, as is confirmed by the persistent presence of high values of citrulline even in the presence of specific inhibitors of the two types of NOS (Table 3).

EXAMPLE 3

4 patients were treated, suffering from pouchitis, a non-specific inflammation of the ileal reservoir, which is most frequently complicated in the long term by the occurrence of ileo-ano-anastomosis for ulcerative colitis. It has recently been suggested that pouchitis is the result of inflammatory NO-mediated damage. The subjects, all volunteers, were treated for 2 months with a lyophilised preparation of *L. brevis* CD2 at a concentration of $5 \times 10^{10}$ CFU/gr, by mouth, at a dosage of 6 g/day. Before and after the treatment a biopsy sample was taken from the mucous membrane of the pouch, which was subjected to homogenisation and then to dosage of the citrulline by means of analysis of the conversion of radio-marked arginine into citrulline.

TABLE 4

Effect of the treatment with CD2 on the activity of inducible nitric oxide synthase in intestinal biopsies of patients with pouchitis

| Patients | Citrulline (pmol/mg proteins/min) | |
|---|---|---|
|  | T0 | T1 |
| 1 | 2.95 | 0.89 |
| 2 | 1.15 | 0.56 |
| 3 | 0.56 | 0.5 |
| 4 | 0.47 | 0.28 |
| 5 | 0.7 | 0.5 |

The treatment with CD2 afforded a significant reduction in the levels of activity of inducible nitric oxide synthase.

The invention claimed is:

1. A method of treating intestinal malabsorption and pancreatic insufficiency with modulation of the metabolic and/or nutritional state in a subject, said method comprising administering to a subject in need thereof an effective amount of *Lactobacillus brevis* CD2 deposited with the DSM-Deutsche Sammlung von Mikroorganismen und Zelikulturen GmbH, Brunswick, Germany, under the access number DSM 11988, having an activity of arginine deiminase expressed as picomols citrulline/mg bacterial proteins/min of not less than 0.1 and their descendants, mutants and derivatives which possess said activity.

2. The method according to claim 1 wherein the bacteria are administered in combination with at least one of *Lactobacillus acidophilus, Lactobacillus buchneri, Lactobacillus casei, Lactobacillus catenaforme, Lactobacillus cellobiosus, Lactobacillus crispatus, Lactobacillus curvatus, Lactobacillus delbrueckii, Lactobacillus jensenii, Lactobacillus leichmanii, Lactobacillus minutus, Lactobacillus plantarum, Lactobacillus rogosae, Lactobacillus salivarius, Bifidobacterium adolescentis, Bifidobacterium angulatum, Bifidobacterium bifidum, Bifidobacterium breve, Bifidobacterium catenulatum, Bifidobacterium dentium, Bifidobacterium eriksonii, Bifidobacterium infantis, Bifidobacterium ion gum, Bifidobacterium plantarum, Bifidobacterium pseudo-catenulatum, Bifidobacterium pseudolongum, Streptococcus lactis, Streptococcus raffinolactis, Streptococcus thermophilus, Acidaminococcus fermenta, Cytophaga fermentans, Rhodoferax fermentans, Cellulomonas fermentans* and *Zymomonas mobilis* and/or in combination with arginine deiminase, sphingomyelinase or other enzymes, with cortisone, anti-inflammatory, immuno-modulant, cytostatic, immunological, endocrinological, vascular, anaesthetic, and vasodilatory drugs, growth factors, cytokines, ceramides, vitamins and minerals, lipids, amino acids and carbohydrates, formulations for enteric use and dietetic, prebiotic or probiotic supplements, and with pharmacologically or dietetically acceptable excipients.

3. The method according to claim 1 wherein the bacteria are lyophilised or sonicated.

4. A method of inducing apoptosis and/or reducing an inflammatory reaction or treating pancreatic insufficiency, said method comprising administering to a subject in need of same an effective amount of A biologically pure strain of *Lactobacillus brevis* CD2 deposited with the DSM-Deutsche Sammlung von Mikroorganismen und Zellkulturen GmbH, Brunswick, Germany, under the access number DSM 11988, having an activity of arginine deiminase expressed as picomols citrulline/mg bacterial proteins/mm of not less than 0.1 and their descendants, mutants and derivatives which possess said activity.

5. The method of claim 4 wherein said strain is administered in combination with *Lactobacillus acidophilus, Lactobacillus buchneri, Lactobacillus casei, Lactobacillus catenaforme, Lactobacillus cellobiosus, Lactobacillus crispatus, Lactobacillus curvatus, Lactobacillus delbrueckii, Lactobacillus jensenii, Lactobacillus leichmanii, Lactobacillus minutus, Lactobacillus plantarum Lactobacillus rogosae, Lactobacillus salivarius, Bifidobacterium adolescentis, Bifidobacterium angulatum, Bifidobacterium bifidum, Bifidobacterium breve, Bifidobacterium catenulatum, Bifidobacterium dentium, Bifidobacterium eriksonii, Bifidobacterium infantis, Bifidobacterium ongum, Bifidobacterium plantarum, Bifidobacterium pseudo-catenulatum, Bifidobacterium pseudolongum, Streptococcus lactis, Streptococcus raffinolactis, Streptococcus thermophilus, Acidaminococcus fermenta, Cytophaga fermentans, Rhodoferax fermentans, Cellulomonas fermentans* and *Zymomonas mobilis* or in association with arginine deiminase, sphingomyelinase or other enzymes, with cortisone, anti-inflammatory, immuno-modulant, cytostatic, immunological, endocrinological, vascular, anaesthetic, vasodilatory drugs, growth factors, cytokines, ceramides, vitamins, minerals, lipids, amino acids, carbohydrates, formulations for enteric use, dietetic, prebiotic or probiotic supplements, and with pharmacologically or dietetically acceptable excipients.

6. A method of reducing inflammation or treating gingivitis or treating periodontopathy comprising administering to a subject in need thereof an effective amount of a *Lactobacillus brevis* CD2 deposited with the DSM-Deutsche Sammlung von Mikroorganismen und Zelikuluren GmbH, Brunswick, Germany, under the access number DSM 11988, having an activity of arginine deiminase expressed as picomols citrulline/mg bacterial proteins/min of not less than 0.1 and their descendants, mutants and derivatives which possess said activity.

7. The method of claim 6 wherein a sphingomyelinase is administered in combination with said *Lactobacillus brevis*.

* * * * *